US011207478B2

(12) United States Patent
Sebastian et al.

(10) Patent No.: US 11,207,478 B2
(45) Date of Patent: Dec. 28, 2021

(54) AEROSOL PRODUCTION ASSEMBLY INCLUDING SURFACE WITH MICRO-PATTERN

(71) Applicant: RAI Strategic Holdings, Inc., Winston-Salem, NC (US)

(72) Inventors: Andries Don Sebastian, Clemmons, NC (US); Michael F. Davis, Clemmons, NC (US); Ercilia Hernandez Garcia, Clayton, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 58 days.

(21) Appl. No.: 15/081,593

(22) Filed: Mar. 25, 2016

(65) Prior Publication Data

US 2017/0273356 A1   Sep. 28, 2017

(51) Int. Cl.
*A24F 47/00* (2020.01)
*A61M 15/06* (2006.01)
(Continued)

(52) U.S. Cl.
CPC ............ *A61M 15/06* (2013.01); *A24F 40/40* (2020.01); *A24F 40/70* (2020.01); *A61M 11/042* (2014.02);
(Continued)

(58) Field of Classification Search
CPC ............ B29C 33/3842; B29C 33/424; A41D 31/0077; B29K 2995/0093;
(Continued)

(56) References Cited

U.S. PATENT DOCUMENTS

| 1,771,366 A | 7/1930 | Wyss et al. |
| 2,057,353 A | 10/1936 | Whittemore, Jr. |

(Continued)

FOREIGN PATENT DOCUMENTS

| AU | 276250 | 7/1965 |
| CA | 2 641 869 | 5/2010 |

(Continued)

OTHER PUBLICATIONS

Vincent, Julian F V et al. "Biomimetics: its practice and theory." Journal of the Royal Society, Interface vol. 3,9 (2006): 471-82. doi: 10.1098/rsif.2006.0127 (Year: 2006).*

(Continued)

*Primary Examiner* — Eric Yaary
(74) *Attorney, Agent, or Firm* — Womble Bond Dickinson (US) LLP

(57) ABSTRACT

The present disclosure relates to an aerosol production assembly. The aerosol production assembly may include a reservoir that contains an aerosol precursor composition and an atomizer that receives the aerosol precursor composition from the reservoir and heats the aerosol precursor composition to produce an aerosol. The aerosol production assembly may additionally include a body that directs the aerosol through an outlet. The body may include a surface including a micro-pattern that defines at least one of hydrophobic and anti-microbial properties. The surface including the micro-pattern may not include a chemical coating that provides these properties. Rather, the surface may define a three-dimensional structure that provides hydrophobic and/or anti-microbial properties. A related assembly method is also provided.

16 Claims, 10 Drawing Sheets

(51) Int. Cl.
  *A61M 11/04* (2006.01)
  *A24F 40/40* (2020.01)
  *A24F 40/70* (2020.01)
  *B29C 33/38* (2006.01)
  *B29C 33/42* (2006.01)
  *B29C 59/02* (2006.01)
  *A61M 15/00* (2006.01)
  *A24F 40/10* (2020.01)
  *B29L 31/00* (2006.01)

(52) U.S. Cl.
  CPC ........ *B29C 33/3842* (2013.01); *B29C 33/424* (2013.01); *B29C 59/02* (2013.01); *A24F 40/10* (2020.01); *A61M 15/0021* (2014.02); *B29K 2995/0093* (2013.01); *B29L 2031/7414* (2013.01)

(58) Field of Classification Search
  CPC .. B29L 2031/7414; A24F 40/10; A24F 40/40; A24F 40/42; A24F 40/70
  See application file for complete search history.

(56) References Cited

U.S. PATENT DOCUMENTS

| | | |
|---|---|---|
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,366,826 A | 1/1983 | Horsewell |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,709,227 A | 1/1998 | Arzonico et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,290,685 B1 | 9/2001 | Insley et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 6,997,244 B2 | 2/2006 | Hul-Chun |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 8,851,081 B2 | 10/2014 | Fernando et al. |
| 8,895,438 B2* | 11/2014 | Peter ............... G03F 7/0002 264/293 |
| 8,997,672 B2 | 4/2015 | Brennan et al. |
| 9,198,462 B2 | 12/2015 | Ghanavi |
| 9,220,302 B2 | 12/2015 | DePiano et al. |
| 9,427,908 B2* | 8/2016 | Low .............. B29C 59/022 |
| 9,908,274 B2* | 3/2018 | Hulseman ........... B21C 23/06 |
| 2002/0146242 A1 | 10/2002 | Vieira |
| 2003/0096083 A1* | 5/2003 | Morgan ............... B05D 5/08 428/141 |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0003146 A1* | 1/2005 | Spath ............... A63C 5/04 428/105 |
| 2005/0016550 A1 | 1/2005 | Katase |
| 2005/0077030 A1 | 4/2005 | Wong |
| 2005/0170098 A1* | 8/2005 | Baumann ............ B08B 17/06 427/372.2 |
| 2005/0181195 A1* | 8/2005 | Dubrow ............. B05D 1/185 428/297.4 |
| 2005/0252508 A1* | 11/2005 | Koerner ........... A61M 15/0065 128/200.14 |
| 2006/0016453 A1 | 1/2006 | Kim |
| 2006/0024504 A1* | 2/2006 | Nelson ............... B29C 59/16 428/409 |
| 2006/0196518 A1 | 9/2006 | Hon |
| 2006/0292345 A1* | 12/2006 | Dave ................ C03C 17/001 428/141 |
| 2007/0074734 A1 | 4/2007 | Braunshteyn et al. |
| 2007/0102013 A1 | 5/2007 | Adams et al. |
| 2007/0157839 A1* | 7/2007 | Kim ................ G02B 5/003 101/483 |
| 2007/0202258 A1 | 8/2007 | Yamagata et al. |
| 2007/0215167 A1 | 9/2007 | Crooks et al. |
| 2007/0231542 A1 | 10/2007 | Deng et al. |
| 2008/0085103 A1 | 4/2008 | Beland et al. |
| 2008/0092912 A1 | 4/2008 | Robinson et al. |
| 2008/0118772 A1* | 5/2008 | Doye ............... B08B 17/06 428/689 |
| 2008/0257367 A1 | 10/2008 | Paterno et al. |
| 2008/0276947 A1 | 11/2008 | Martzel |
| 2008/0302374 A1 | 12/2008 | Wengert et al. |

(56) References Cited

U.S. PATENT DOCUMENTS

| | | |
|---|---|---|
| 2009/0011222 A1* | 1/2009 | Xiu .................... C23C 18/00 428/323 |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0126404 A1 | 5/2010 | Brennan et al. |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0229667 A1* | 9/2011 | Jin .................... B81C 1/00206 428/34.1 |
| 2011/0265806 A1 | 11/2011 | Alarcon et al. |
| 2011/0275912 A1* | 11/2011 | Boyden ................ A61L 2/0011 600/309 |
| 2011/0277780 A1 | 11/2011 | Terry et al. |
| 2011/0287203 A1* | 11/2011 | Victor ................. B29C 37/0053 428/36.9 |
| 2011/0309157 A1 | 12/2011 | Yang et al. |
| 2012/0000480 A1 | 1/2012 | Sebastian et al. |
| 2012/0034390 A1 | 2/2012 | Suh et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |
| 2013/0255702 A1 | 10/2013 | Griffith, Jr. et al. |
| 2013/0306064 A1 | 11/2013 | Thorens et al. |
| 2013/0306065 A1 | 11/2013 | Thorens et al. |
| 2013/0306066 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261492 A1 | 9/2014 | Kane et al. |
| 2014/0261495 A1 | 9/2014 | Novak, III et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0283859 A1* | 9/2014 | Minskoff .............. A24F 47/008 131/329 |
| 2014/0342121 A1* | 11/2014 | Taguchi ................ G02B 1/105 428/141 |
| 2014/0345631 A1 | 11/2014 | Bowen et al. |
| 2015/0007838 A1 | 1/2015 | Fernando et al. |
| 2015/0027456 A1 | 1/2015 | Janardhan et al. |
| 2015/0053217 A1 | 2/2015 | Steingraber et al. |
| 2015/0114411 A1 | 4/2015 | Buchberger |
| 2015/0136158 A1 | 5/2015 | Stevens et al. |
| 2015/0181928 A1 | 7/2015 | Liu |
| 2015/0231821 A1* | 8/2015 | Heiskanen ............ B29C 59/022 428/211.1 |
| 2015/0251201 A1* | 9/2015 | Hradetzky ............ A61M 11/00 239/690 |
| 2016/0000149 A1 | 1/2016 | Scatterday |
| 2016/0037826 A1 | 2/2016 | Hearn et al. |
| 2016/0052177 A1* | 2/2016 | Chauvin ................ B29C 49/12 264/524 |
| 2016/0121057 A1* | 5/2016 | Dyche ...................... B05B 1/08 128/200.23 |
| 2016/0228658 A1* | 8/2016 | Minskoff .............. A61M 15/02 |
| 2016/0229095 A1* | 8/2016 | Mori ...................... G02B 1/118 |
| 2016/0270442 A1 | 9/2016 | Liu |
| 2016/0271347 A1* | 9/2016 | Raichman ........... A24F 47/008 |
| 2017/0042243 A1* | 2/2017 | Plojoux ................ A24F 47/008 |
| 2017/0050343 A1* | 2/2017 | Wei ...................... B29C 33/3892 |
| 2017/0136660 A1* | 5/2017 | Heilmann ............ B29C 33/3842 |
| 2017/0144202 A1* | 5/2017 | King .................... B08B 17/065 |
| 2017/0309364 A1* | 10/2017 | Yamada .................... H01B 1/22 |
| 2017/0311452 A1* | 10/2017 | Ho ........................ H05K 3/1258 |
| 2017/0312458 A1* | 11/2017 | Beller .................. A61M 15/0008 |
| 2017/0367402 A1 | 12/2017 | Lau et al. |

FOREIGN PATENT DOCUMENTS

| | | |
|---|---|---|
| CN | 2571179 | 9/2003 |
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| CN | 103504481 | 1/2014 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 187 263 | 5/2010 |
| EP | 2 316 286 | 5/2011 |
| EP | 2 460 422 A1 | 6/2012 |
| GB | 2469850 | 11/2010 |
| RU | 2564611 | 10/2015 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2011/094344 | 8/2011 |
| WO | 2011/117580 A2 | 9/2011 |
| WO | WO 2012/072762 | 6/2012 |
| WO | WO 2012/100523 | 8/2012 |
| WO | WO 2013/089551 | 6/2013 |

(56) References Cited

FOREIGN PATENT DOCUMENTS

| WO | WO 2015/013329 | 1/2015 |
|---|---|---|
| WO | 2015189623 A1 | 12/2015 |
| WO | WO 2016/042409 | 3/2016 |

OTHER PUBLICATIONS

International Search Report dated Jun. 29, 2017 in corresponding application No. PCT/IB2017/051699 filed Mar. 23, 2017.
Sanjay S. Latthe et al.,"Superhydrophobic Surfaces Developed by Mimicking Hierarchical Surface Morphology of Lotus Leaf", Molecules, Apr. 4, 2014, vol. 19, ISSN 1420-3049, http://www.mdpi.com/1420-3049/19/4/4256/pdf, pp. 4256-4283.
S. Lee et al., "Artificial Lotus Leaf Structures Made by Blasting with Sodium Bicarbonate", 18$^{th}$ International Conference on Composite Materials, http://www.iccm-central.org/Proceedings/ICCM18proceedings/data/2.%20Oral%20Presentation/Aug22%28Monday%29/M24%, pp. 1-5, Retrieved 25, 2016.
"The Technology of Sharklet", Sharklet Technologies, Inc., http://sharklet.com/our-technology/technology-overview/, pp. 1-2, Retrieved Mar. 25, 2016.
Koch, K. et al., "Diversity of structure, morphology and wetting of plant surfaces," *Soft Matter*, 2008, vol. 4, pp. 1943-1963.
Koch, K. et al., "Multifunctional surface structures of plants: An inspiration for biomimetics," *Progress in Materials Science*, 2009, vol. 54, pp. 137-178.

\* cited by examiner

1002 — PROVIDE AN AEROSOL PRECURSOR COMPOSITION

1004 — POSITION AN ATOMIZER IN FLUID COMMUNICATION WITH THE AEROSOL PRECURSOR COMPOSITION

1006 — ASSEMBLE THE ATOMIZER WITH A BODY COMPRISING A SURFACE OF WHICH AT LEAST A PORTION INCLUDES A MICRO-PATTERN IMPARTING AT LEAST ONE OF HYDROPHOBIC AND ANTI-MICROBIAL PROPERTIES

FIG. 10

1102 — PROVIDE AN AEROSOL DELIVERY DEVICE WITH A SURFACE OF WHICH AT LEAST A PORTION INCLUDES A MICRO-PATTERN IMPARTING AT LEAST ONE OF HYDROPHOBIC AND ANTI-MICROBIAL PROPERTIES

FIG. 11

AEROSOL PRODUCTION ASSEMBLY INCLUDING SURFACE WITH MICRO-PATTERN

BACKGROUND

Field of the Disclosure

The present disclosure relates to aerosol delivery devices such as electronic cigarettes, and more particularly to aerosol delivery devices including an atomizer and an antimicrobial surface. The atomizer may be configured to heat an aerosol precursor composition, which may be made or derived from tobacco or otherwise incorporate tobacco, to form an inhalable substance for human consumption.

Description of Related Art

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., and U.S. Pat. App. Pub. No. 2015/0059780 to Davis et al., which are incorporated herein by reference in their entireties. See also, for example, the various embodiments of products and heating configurations described in the background sections of U.S. Pat. No. 5,388,594 to Counts et al. and U.S. Pat. No. 8,079,371 to Robinson et al., which are incorporated by reference in their entireties.

Usage of aerosol delivery devices involves inhaling aerosol produced by the aerosol delivery device. A user typically places the aerosol delivery device against his or her lips to draw on the aerosol delivery device and receive the aerosol. However, such usage may expose the aerosol delivery device to saliva and/or other biological matter. Accordingly, it may be desirable to provide the aerosol delivery device with features configured to resist microbial growth.

BRIEF SUMMARY OF THE DISCLOSURE

The present disclosure relates to assembly of cartridges for aerosol delivery devices configured to produce aerosol and which aerosol delivery devices, in some embodiments, may be referred to as electronic cigarettes. In one aspect, an aerosol production assembly is provided. The aerosol production assembly may include an aerosol precursor composition, an atomizer, and a body. The body may include a surface of which at least a portion may include a micro-pattern imparting at least one of hydrophobic and anti-microbial properties.

In some embodiments the body may include a mouthpiece defining an outlet. The micro-pattern may be a biomimicry micro-pattern. The surface may define a sharkskin micro-pattern or a lotus leaf micro-pattern. The surface may not include a chemical coating. The surface may be positioned at an inner surface of the body. The surface may be positioned at an outer surface of the body.

In some embodiments the body may be formed in a mold configured to define the micro-pattern at the surface. The mold may be etched. The aerosol production assembly may be included in a cartridge or a tank for an aerosol delivery device.

In an additional aspect, a method of forming an aerosol production assembly is provided. The method may include providing an aerosol precursor composition. Further, the method may include positioning an atomizer in fluid communication with the aerosol precursor composition. The method may additionally include assembling the atomizer with a body comprising a surface of which at least a portion includes a micro-pattern imparting at least one of hydrophobic and anti-microbial properties.

In some embodiments assembling the atomizer with the body may include positioning the body in fluid communication with the atomizer. Further, the method may include forming the body including the micro-pattern. Forming the body may not include coating the surface with a chemical.

In some embodiments, forming the body may include forming the micro-pattern at at least one of an inner surface and an outer surface of the body. Forming the body may include forming the micro-pattern in a mold. The method may additionally include etching the mold.

In an additional aspect, a method of improving cleanliness of an aerosol delivery device is provided. The method may include providing the aerosol delivery device with a surface of which at least a portion includes a micro-pattern imparting at least one of hydrophobic and anti-microbial properties. The micro-pattern may be a biomimicry micro-pattern. The surface may define a sharkskin micro-pattern or a lotus leaf micro-pattern.

These and other features, aspects, and advantages of the disclosure will be apparent from a reading of the following detailed description together with the accompanying drawings, which are briefly described below.

BRIEF DESCRIPTION OF THE FIGURES

Figure 1:
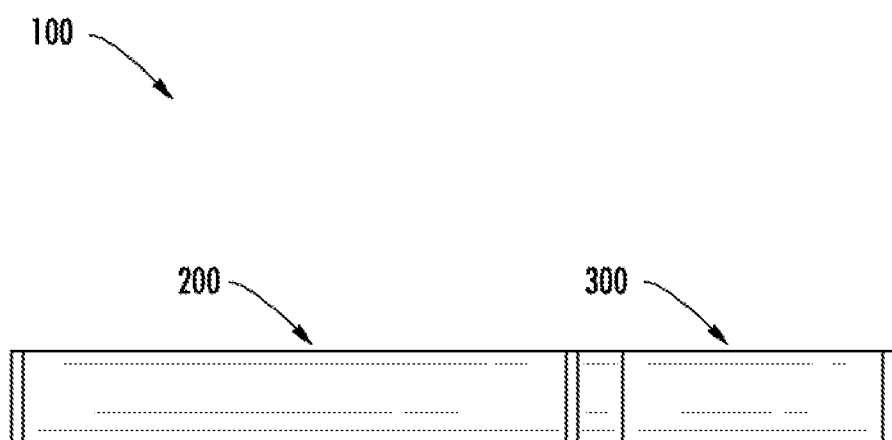
Figure 2:
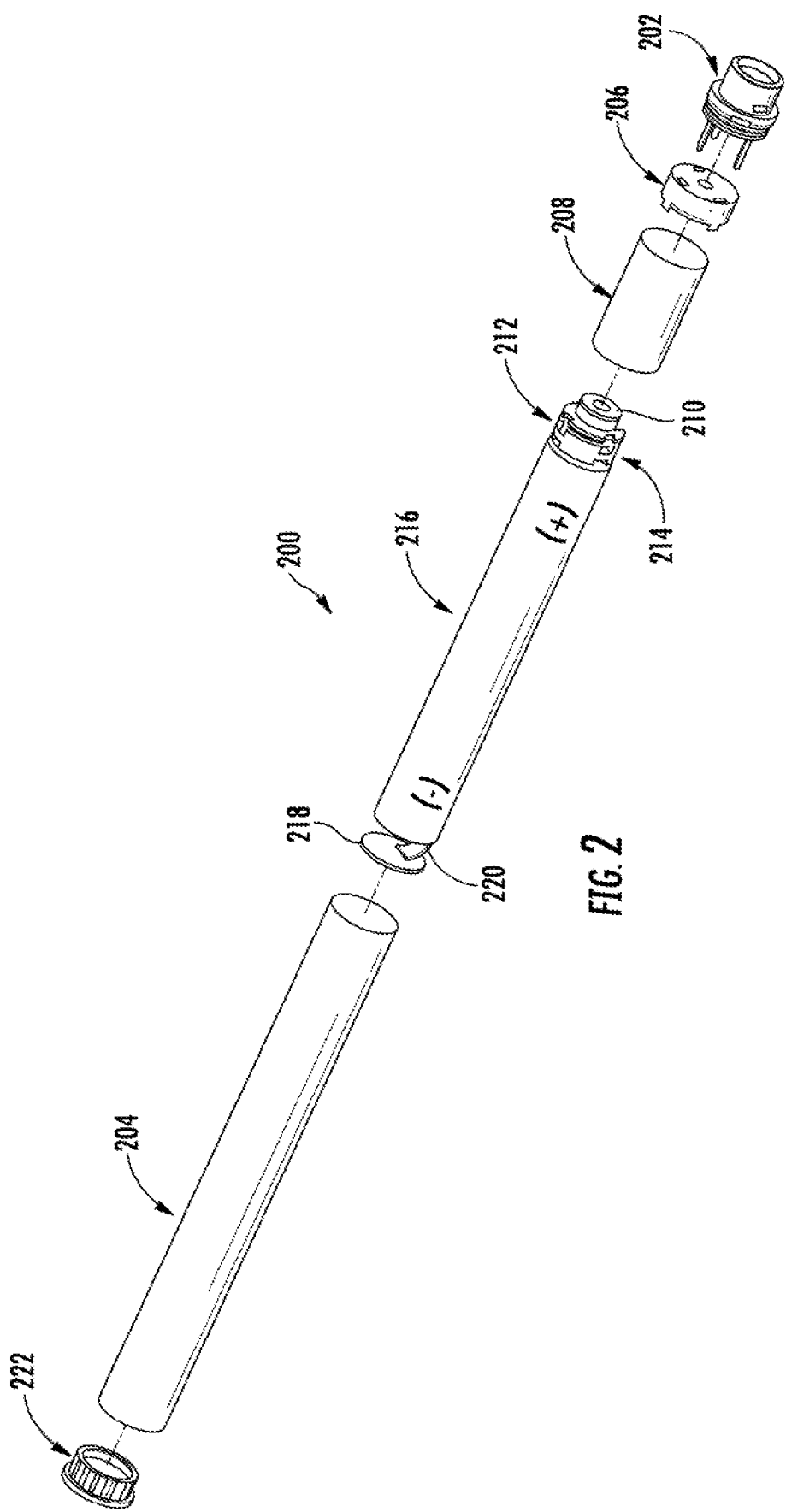
Figure 3:
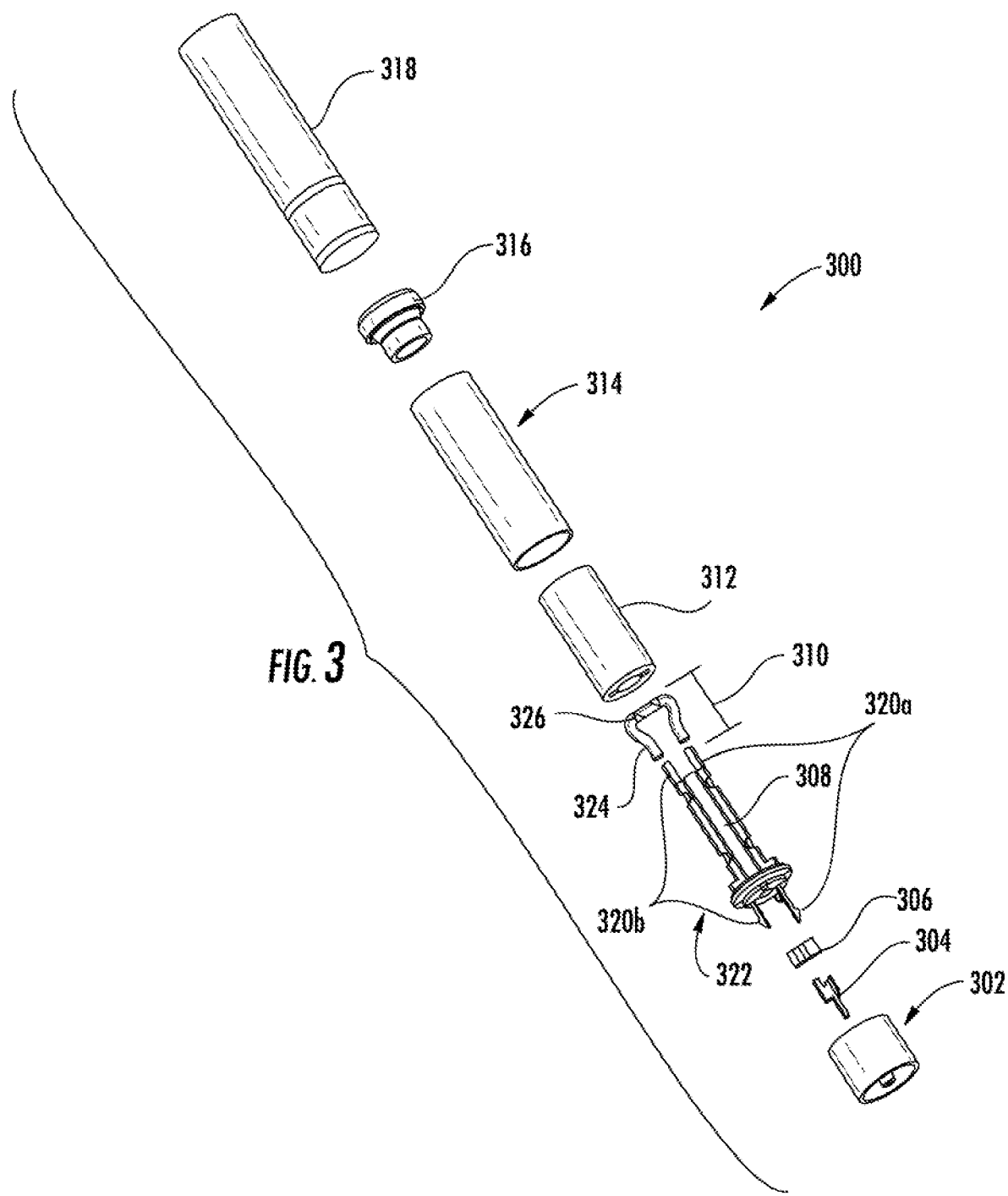
Figure 4:
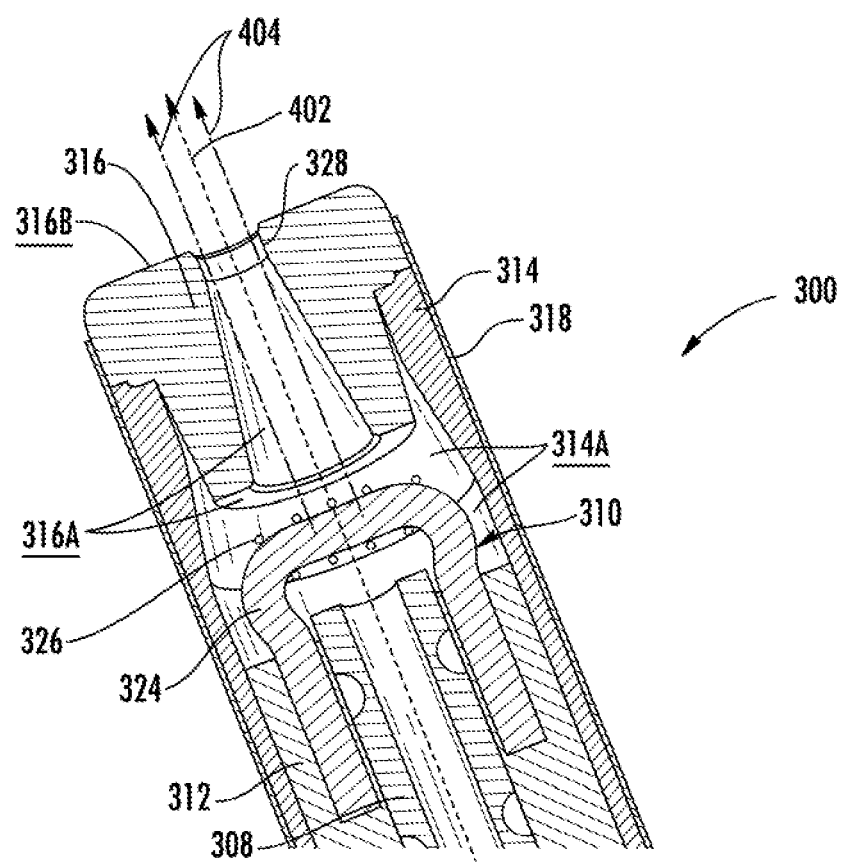
Figure 5:
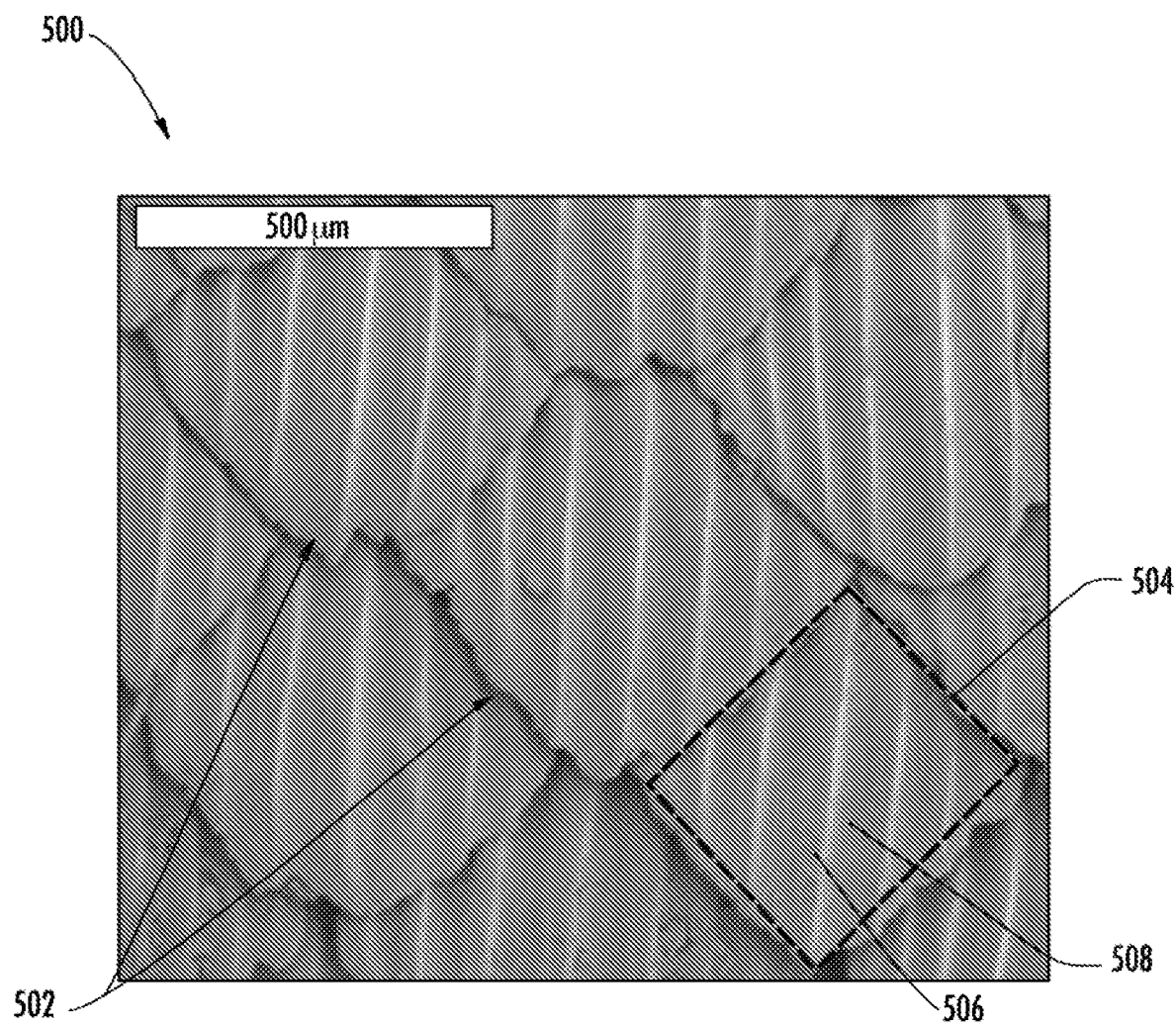
Figure 6:
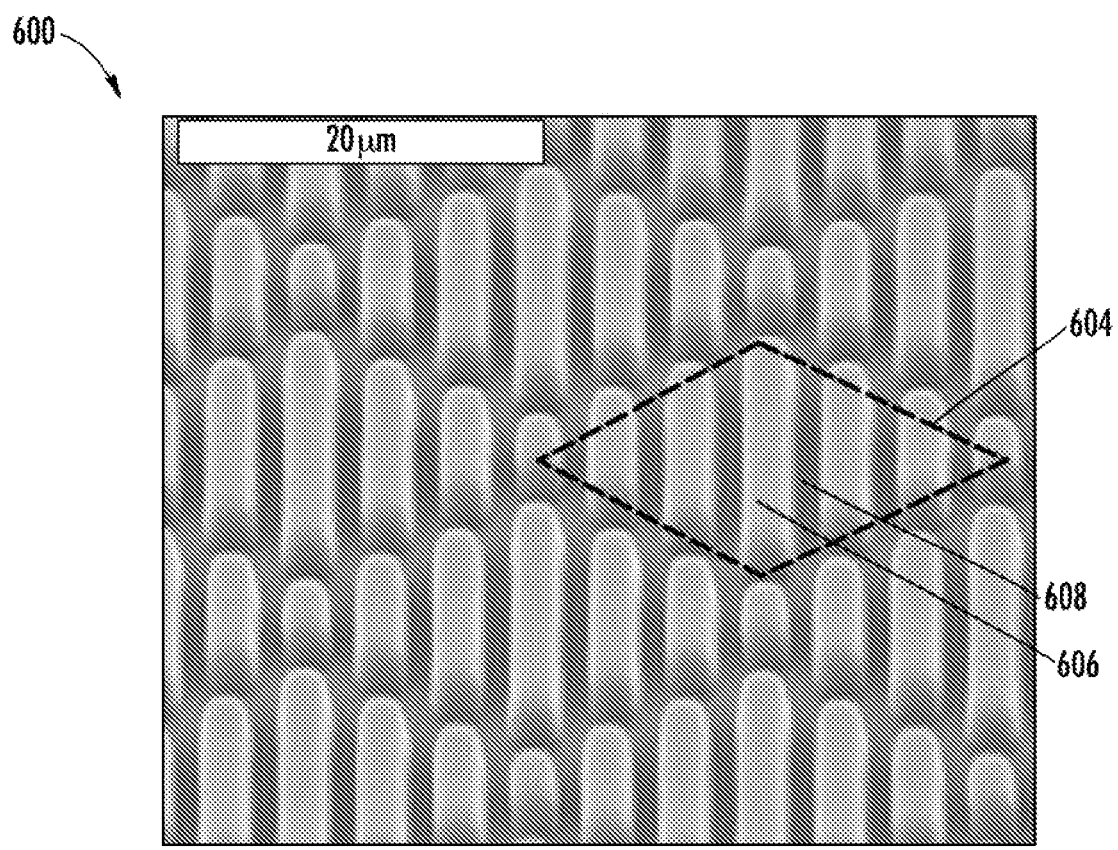
Figure 7:
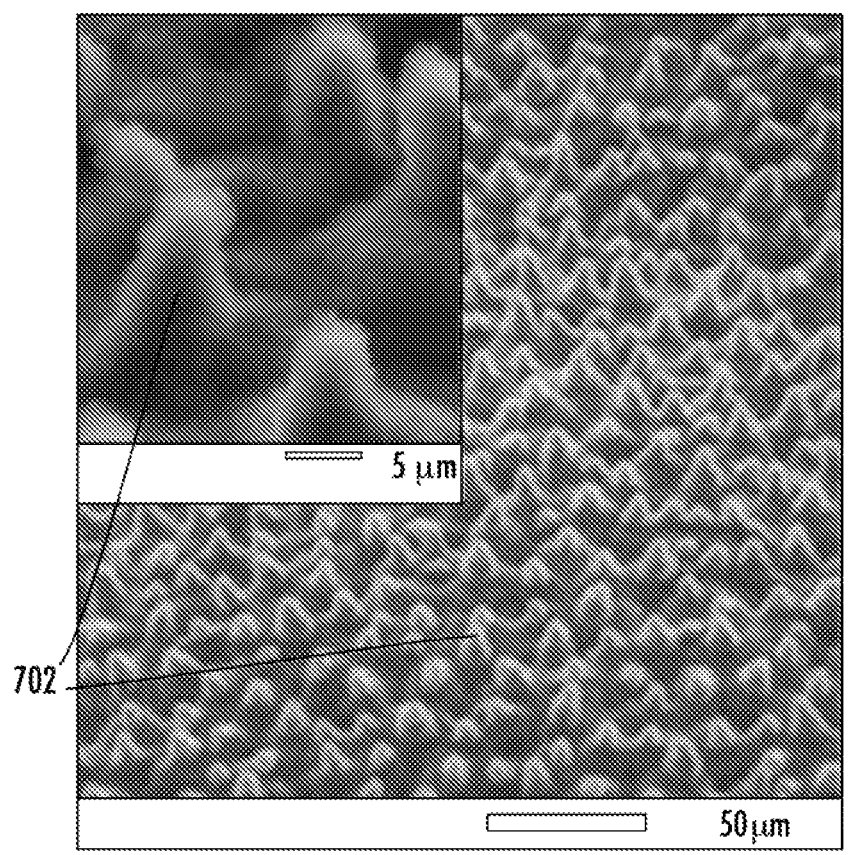
Figure 8:
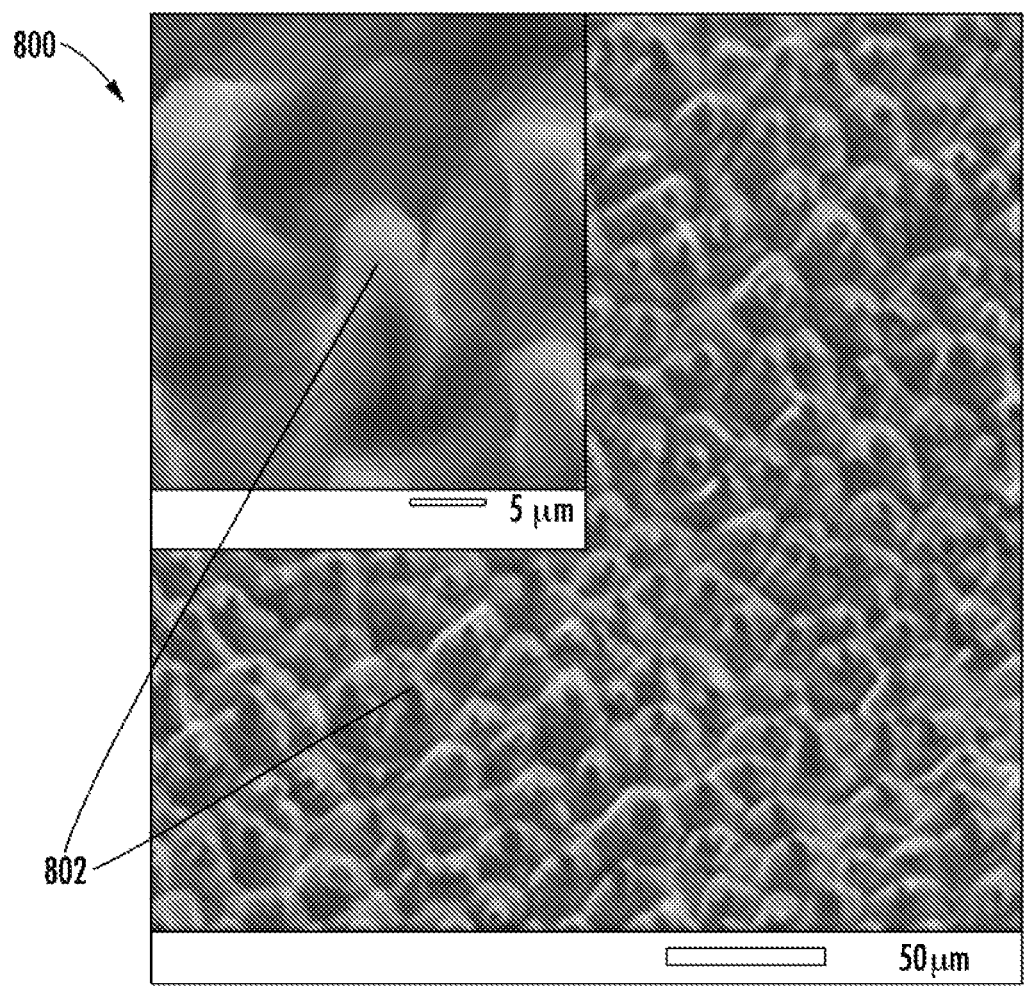
Figure 9:
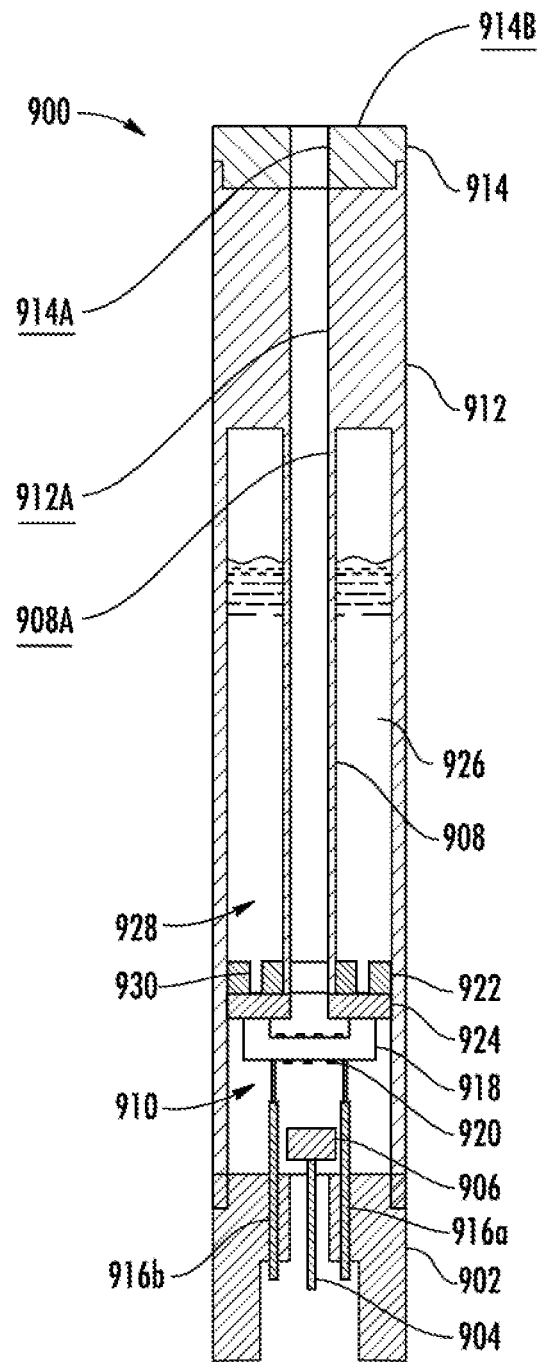

Having thus described the disclosure in the foregoing general terms, reference will now be made to the accompanying drawings, which are not necessarily drawn to scale, and wherein:

FIG. 1 illustrates a side view of an aerosol delivery device comprising a cartridge and a control body in an assembled configuration according to an example embodiment of the present disclosure;

FIG. 2 illustrates the control body of FIG. 1 in an exploded configuration according to an example embodiment of the present disclosure;

FIG. 3 illustrates the cartridge of FIG. 1 in an exploded configuration according to an example embodiment of the present disclosure;

FIG. 4 illustrates a partial sectional view through the cartridge of FIG. 1 according to an example embodiment of the present disclosure;

FIG. 5 illustrates a microscopic image of sharkskin;

FIG. 6 illustrates a microscopic image of a surface including a sharkskin micro-pattern according to an example embodiment of the present disclosure;

FIG. 7 illustrates scanning electron microscopic images of a lotus leaf;

FIG. 8 illustrates scanning electron microscopic images of a surface including a lotus leaf micro-pattern according to an example embodiment of the present disclosure;

FIG. 9 illustrates a sectional view through a tank of an aerosol delivery device according to an example embodiment of the present disclosure;

FIG. 10 schematically illustrates a method for assembling an aerosol delivery device according to an example embodiment of the present disclosure; and FIG. 11 schematically illustrates a method of improving cleanliness of an aerosol delivery device.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

The present disclosure provides descriptions of aerosol delivery devices. The aerosol delivery devices may use electrical energy to heat a material (preferably without combusting the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device most preferably yields vapors (including vapors within aerosols that can be considered to be visible aerosols that might be considered to be described as smoke-like) resulting from volatilization or vaporization of certain components of the article or device, although in other embodiments the aerosol may not be visible. In highly preferred embodiments, aerosol delivery devices may incorporate tobacco and/or components derived from tobacco. As such, the aerosol delivery device can be characterized as an electronic smoking article such as an electronic cigarette or "e-cigarette."

While the present disclosure is generally directed to aerosol delivery devices such as so-called "e-cigarettes," it should be understood that the mechanisms, components, features, and methods may be embodied in many different forms and associated with a variety of articles. For example, the description provided herein may be employed in conjunction with embodiments of traditional smoking articles (e.g., cigarettes, cigars, pipes, etc.) and heat-not-burn cigarettes. Accordingly, it should be understood that the description of the mechanisms, components, features, and methods disclosed herein are discussed in terms of embodiments relating to aerosol delivery mechanisms by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer shell or body. The overall design of the outer shell or body can vary, and the format or configuration of the outer body that can define the overall size and shape of the aerosol delivery device can vary. Typically, an elongated body resembling the shape of a cigarette or cigar can be a formed from a single, unitary shell; or the elongated body can be formed of two or more separable pieces. For example, an aerosol delivery device can comprise an elongated shell or body that can be substantially tubular in shape and, as such, resemble the shape of a conventional cigarette or cigar. However, various other shapes and configurations may be employed in other embodiments (e.g., rectangular or fob-shaped).

In one embodiment, all of the components of the aerosol delivery device are contained within one outer body or shell. Alternatively, an aerosol delivery device can comprise two or more shells that are joined and are separable. For example, an aerosol delivery device can possess at one end a control body comprising a shell containing one or more reusable components (e.g., a rechargeable battery and various electronics for controlling the operation of that article), and at the other end and removably attached thereto a shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various aerosol delivery device designs and component arrangements can be appreciated upon consideration of the commercially available electronic smoking articles.

Aerosol delivery devices of the present disclosure most preferably comprise some combination of a power source (i.e., an electrical power source), at least one control component (e.g., means for actuating, controlling, regulating and/or ceasing power for heat generation, such as by controlling electrical current flow from the power source to other components of the aerosol delivery device), a heater or heat generation component (e.g., an electrical resistance heating element or component commonly referred to as part of an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the article such that aerosol generated can be withdrawn therefrom upon draw).

Alignment of the components within the aerosol delivery device of the present disclosure can vary. In specific embodiments, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery or other electrical power source (e.g., a capacitor) to provide current flow sufficient to provide various functionalities to the aerosol delivery device, such as powering of a heater, powering of control systems, powering of indicators, and the like. The power source can take on various embodiments. Preferably, the power source is able to deliver sufficient power to rapidly heat the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices.

One example embodiment of an aerosol delivery device 100 is illustrated in FIG. 1. In particular, FIG. 1 illustrates an aerosol delivery device 100 including a control body 200 and a cartridge 300. The control body 200 and the cartridge 300 can be permanently or detachably aligned in a functioning relationship. Various mechanisms may connect the cartridge 300 to the control body 200 to result in a threaded engagement, a press-fit engagement, an interference fit, a magnetic engagement, or the like. The aerosol delivery device 100 may be substantially rod-like, substantially tubular shaped, or substantially cylindrically shaped in some embodiments when the cartridge 300 and the control body 200 are in an assembled configuration. However, various other configurations such as rectangular or fob-shaped may be employed in other embodiments.

In specific embodiments, one or both of the cartridge 300 and the control body 200 may be referred to as being disposable or as being reusable. For example, the control body 200 may have a replaceable battery or a rechargeable battery and/or capacitor and thus may be combined with any type of recharging technology, including connection to a typical alternating current electrical outlet, connection to a car charger (i.e., cigarette lighter receptacle), and connection to a computer, such as through a universal serial bus (USB) cable. Further, in some embodiments the cartridge 300 may comprise a single-use cartridge, as disclosed in U.S. Pat. No. 8,910,639 to Chang et al., which is incorporated herein by reference in its entirety.

FIG. 2 illustrates an exploded view of the control body 200 of the aerosol delivery device 100 (see, FIG. 1) according to an example embodiment of the present disclosure. As illustrated, the control body 200 may comprise a coupler 202, an outer body 204, a sealing member 206, an adhesive member 208 (e.g., KAPTON® tape), a flow sensor 210 (e.g., a puff sensor or pressure switch), a control component 212, a spacer 214, an electrical power source 216 (e.g., a battery, which may be rechargeable), a circuit board with an indicator 218 (e.g., a light emitting diode (LED)), a connector circuit 220, and an end cap 222. Examples of electrical power sources are described in U.S. Pat. App. Pub. No. 2010/0028766 by Peckerar et al., the disclosure of which is incorporated herein by reference in its entirety.

With respect to the flow sensor 210, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. App. Pub. No. 2014/0270727 to Ampolini et al., which is incorporated herein by reference in its entirety.

In one embodiment the indicator 218 may comprise one or more light emitting diodes. The indicator 218 can be in communication with the control component 212 through the connector circuit 220 and be illuminated, for example, during a user drawing on a cartridge coupled to the coupler 202, as detected by the flow sensor 210. The end cap 222 may be adapted to make visible the illumination provided thereunder by the indicator 218. Accordingly, the indicator 218 may be illuminated during use of the aerosol delivery device 100 to simulate the lit end of a smoking article. However, in other embodiments the indicator 218 can be provided in varying numbers and can take on different shapes and can even be an opening in the outer body (such as for release of sound when such indicators are present).

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; and U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; WO 2010/091593 to Hon; and WO 2013/089551 to Foo, each of which is incorporated herein by reference in its entirety. A variety of the materials disclosed by the foregoing documents may be incorporated into the present devices in various embodiments, and all of the foregoing disclosures are incorporated herein by reference in their entireties.

FIG. 3 illustrates the cartridge 300 in an exploded configuration. As illustrated, the cartridge 300 may comprise a base 302, a control component terminal 304, an electronic control component 306, a flow director 308, an atomizer 310, a reservoir such as a container and/or a reservoir substrate 312, an outer body 314, a mouthpiece 316, a label 318, and first and second heating terminals 320a, 320b according to an example embodiment of the present disclosure.

In some embodiments the first and second heating terminals 320a, 320b may be embedded in, or otherwise coupled to, the flow director 308. For example, the first and second heating terminals 320a, 320b may be insert molded in the flow director 308. Accordingly, the flow director 308 and the first and second heating terminals may be collectively referred to as a flow director assembly 322. Additional description with respect to the first and second heating terminals 320a, 320b and the flow director 308 is provided in U.S. Pat. Pub. No. 2015/0335071 to Brinkley et al., which is incorporated herein by reference in its entirety.

The atomizer 310 may comprise a liquid transport element 324 and a heating element 326. The cartridge may additionally include a base shipping plug engaged with the base and/or a mouthpiece shipping plug engaged with the mouthpiece in order to protect the base and the mouthpiece and prevent entry of contaminants therein prior to use as disclosed, for example, in U.S. Pat. No. 9,220,302 to Depiano et al., which is incorporated herein by reference in its entirety.

The base 302 may be coupled to a first end of the outer body 314 and the mouthpiece 316 may be coupled to an opposing second end of the outer body to substantially or fully enclose other components of the cartridge 300 therein. For example, the control component terminal 304, the electronic control component 306, the flow director 308, the atomizer 310, and the reservoir substrate 312 may be substantially or entirely retained within the outer body 314. The label 318 may at least partially surround the outer body 314, and optionally the base 302, and include information such as a product identifier thereon. The base 302 may be configured to engage the coupler 202 of the control body 200 (see, e.g., FIG. 2). In some embodiments the base 302 may comprise anti-rotation features that substantially prevent relative rotation between the cartridge and the control body as disclosed in U.S. Pat. App. Pub. No. 2014/0261495 to Novak et al., which is incorporated herein by reference in its entirety.

The reservoir substrate 312 may be configured to hold an aerosol precursor composition. Representative types of aerosol precursor components and formulations are also set forth and characterized in U.S. Pat. No. 7,726,320 to Robinson et al.; U.S. Pat. No. 8,881,737 to Collett et al.; and U.S. Pat. No. 9,254,002 to Chong et al., and U.S. Pat. Pub. Nos. 2013/0008457 to Zheng et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC. Embodiments of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al; and U.S. Pat. No. 8,627,828 to Strickland et al.; as well as US Pat. Pub. Nos. 2010/0018539 to Brinkley et al. and 2010/0170522 to Sun et al.; and PCT WO 97/06786 to Johnson et al., all of which are incorporated by reference herein.

The reservoir substrate 312 may comprise a plurality of layers of nonwoven fibers formed into the shape of a tube encircling the interior of the outer body 314 of the cartridge 300. Thus, liquid components, for example, can be sorptively retained by the reservoir substrate 312. The reservoir substrate 312 is in fluid connection with the liquid transport element 324. Thus, the liquid transport element 324 may be configured to transport liquid from the reservoir substrate 312 to the heating element 326 via capillary action or other liquid transport mechanisms.

As illustrated, the liquid transport element 324 may be in direct contact with the heating element 326. As further illustrated in FIG. 3, the heating element 326 may comprise a wire defining a plurality of coils wound about the liquid transport element 324. In some embodiments the heating element 326 may be formed by winding the wire about the liquid transport element 324 as described in U.S. Pat. No. 9,210,738 to Ward et al., which is incorporated herein by reference in its entirety. Further, in some embodiments the wire may define a variable coil spacing, as described in U.S. Pat. App. Pub. No. 2014/0270730 to DePiano et al., which is incorporated herein by reference in its entirety. Various embodiments of materials configured to produce heat when electrical current is applied therethrough may be employed to form the heating element 326. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), titanium, platinum, silver, palladium, graphite and graphite-based materials; and ceramic (e.g., a positive or negative temperature coefficient ceramic).

However, various other embodiments of methods may be employed to form the heating element 326, and various other embodiments of heating elements may be employed in the atomizer 310. For example, a stamped heating element may be employed in the atomizer, as described in U.S. Pat. App. Pub. No. 2014/0270729 to DePiano et al., which is incorporated herein by reference in its entirety. Further to the above, additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other embodiments. Various additional examples of heaters and materials employed to form heaters are described in U.S. Pat. No. 8,881,737 to Collett et al., which is incorporated herein by reference, as noted above.

A variety of heater components may be used in the present aerosol delivery device. In various embodiments, one or more microheaters or like solid state heaters may be used. Microheaters and atomizers incorporating microheaters suitable for use in the presently disclosed devices are described in U.S. Pat. No. 8,881,737 to Collett et al., which is incorporated herein by reference in its entirety.

The first heating terminal 320a and the second heating terminal 320b (e.g., negative and positive heating terminals) are configured to engage opposing ends of the heating element 326 and to form an electrical connection with the control body 200 (see, e.g., FIG. 2) when the cartridge 300 is connected thereto. Further, when the control body 200 is coupled to the cartridge 300, the electronic control component 306 may form an electrical connection with the control body 200 through the control component terminal 304. The control body 200 may thus employ the electronic control component 212 (see, FIG. 2) to determine whether the cartridge 300 is genuine and/or perform other functions.

Further, various examples of electronic control components and functions performed thereby are described in U.S. Pat. App. Pub. No. 2014/0096781 to Sears et al., which is incorporated herein by reference in its entirety.

Various other details with respect to the components that may be included in the cartridge 300, are provided, for example, in U.S. Pat. App. Pub. No. 2014/0261495 to DePiano et al., which is incorporated herein by reference in its entirety. In this regard, FIG. 7 thereof illustrates an enlarged exploded view of a base and a control component terminal; FIG. 8 thereof illustrates an enlarged perspective view of the base and the control component terminal in an assembled configuration; FIG. 9 thereof illustrates an enlarged perspective view of the base, the control component terminal, an electronic control component, and heating terminals in an assembled configuration; FIG. 10 thereof illustrates an enlarged perspective view of the base, the atomizer, and the control component in an assembled configuration; FIG. 11 thereof illustrates an opposing perspective view of the assembly of FIG. 10 thereof; FIG. 12 thereof illustrates an enlarged perspective view of the base, the atomizer, the flow director, and the reservoir substrate in an assembled configuration; FIG. 13 thereof illustrates a perspective view of the base and an outer body in an assembled configuration; FIG. 14 thereof illustrates a perspective view of a cartridge in an assembled configuration; FIG. 15 thereof illustrates a first partial perspective view of the cartridge of FIG. 14 thereof and a coupler for a control body; FIG. 16 thereof illustrates an opposing second partial perspective view of the cartridge of FIG. 14 thereof and the coupler of FIG. 15 thereof; FIG. 17 thereof illustrates a perspective view of a cartridge including a base with an anti-rotation mechanism; FIG. 18 thereof illustrates a perspective view of a control body including a coupler with an anti-rotation mechanism; FIG. 19 thereof illustrates alignment of the cartridge of FIG. 17 with the control body of FIG. 18; FIG. 20 thereof illustrates an aerosol delivery device comprising the cartridge of FIG. 17 thereof and the control body of FIG. 18 thereof with a modified view through the aerosol delivery device illustrating the engagement of the anti-rotation mechanism of the cartridge with the anti-rotation mechanism of the connector body; FIG. 21 thereof illustrates a perspective view of a base with an anti-rotation mechanism; FIG. 22 thereof illustrates a perspective view of a coupler with an anti-rotation mechanism; and FIG. 23 thereof illustrates a sectional view through the base of FIG. 21 thereof and the coupler of FIG. 22 thereof in an engaged configuration. Various other details with respect to the components that may be included in the cartridge 300, are provided, for example, in U.S. Pat. Pub. No. 2015/0335071 to Brinkley et al., filed May 23, 2014, which is incorporated herein by reference in its entirety.

Various components of an aerosol delivery device according to the present disclosure can be chosen from components described in the art and commercially available. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety.

In another embodiment substantially the entirety of the cartridge may be formed from one or more carbon materials, which may provide advantages in terms of biodegradability and absence of wires. In this regard, the heating element may comprise carbon foam, the reservoir substrate may comprise carbonized fabric, and graphite may be employed to form an electrical connection with the power source and control component. An example embodiment of a carbon-based cartridge is provided in U.S. Pat. App. Pub. No. 2013/0255702 to Griffith et al., which is incorporated herein by reference in its entirety.

During use, a user may draw on the mouthpiece 316 of the cartridge 300 of the aerosol delivery device 100 (see, FIG. 1). This may pull air through an opening in the control body 200 (see, e.g., FIG. 2) or in the cartridge 300. For example, in one embodiment an opening may be defined between the coupler 202 and the outer body 204 of the control body 200 (see, e.g., FIG. 2), as described in U.S. Pat. No. 9,220,302 to DePiano et al., which is incorporated herein by reference in its entirety. However, the flow of air may be received through other parts of the aerosol delivery device 100 in other embodiments. As noted above, in some embodiments the cartridge 300 may include the flow director 308. The flow director 308 may be configured to direct the flow of air received from the control body 200 to the heating element 326 of the atomizer 310.

A sensor in the aerosol delivery device 100 (e.g., the flow sensor 210 in the control body 200) may sense the puff. When the puff is sensed, the control body 200 may direct current to the heating element 326 through a circuit including the first heating terminal 320a and the second heating terminal 320b. Accordingly, the heating element 326 may vaporize the aerosol precursor composition directed to an aerosolization zone from the reservoir substrate 312 by the liquid transport element 324. In this regard, components of the aerosol delivery device 100 (see, FIG. 1) including at least a reservoir (e.g., the reservoir substrate 312) configured to contain an aerosol precursor composition and an atomizer (e.g., the atomizer 310) may be referred to as an aerosol production assembly. The mouthpiece 316 may allow passage of air and entrained vapor (i.e., the components of the aerosol precursor composition in an inhalable form) from the cartridge 300 through an outlet 328 to a consumer drawing thereon.

Accordingly, when a user draws on the aerosol delivery device 100 (see, FIG. 1), his or her lips may contact a portion thereof, such as the mouthpiece 316. Further, when the user draws on the aerosol delivery device 100, aerosol may be produced inside the aerosol delivery device and directed to the user. However, operation in this manner may result in certain problems.

In this regard, due to repeated contact with a user's lips, the mouthpiece 316 and/or other portions of the aerosol delivery device 100 (see, FIG. 1) may be exposed to a user's breath and saliva and any pathogens therein. By way of further example, in the event that the user exhales into the aerosol delivery device 100, the portions of the aerosol delivery device along the airflow path therethrough may be exposed to such pathogens. Accordingly, microbial growth may occur at the mouthpiece 316 and/or other portions of the aerosol delivery device 100.

Further, some of the aerosol produced in the aerosol delivery device 100 (see, FIG. 1) may condense on the internal surfaces thereof. Fluid droplets may thus form inside the aerosol delivery device 100. In some instances the fluid droplets may exit the aerosol delivery device 100 though the mouthpiece 316 or other aperture leading to the surrounding environment. Thereby, such fluid droplets may undesirably contact surrounding structures, such as a user's pocket when received therein. Further, the liquid droplets are wasted, rather than delivered to the user as an aerosol. This may reduce the efficiency of delivery of aerosol to the user and/or the condensed aerosol may be received by the user in liquid form, which may affect the taste or other sensory characteristics associated with using the aerosol delivery device.

Accordingly, embodiments of the present disclosure may include features configured to address the above-noted problems. In this regard, FIG. 4 illustrates a partial sectional view through the cartridge 300. As illustrated, in one embodiment air 402 may flow through the flow director 308 past the atomizer 310. At least a portion of the air 402 may combine with vapor produced at the atomizer 310 to form aerosol 404, which exits through the mouthpiece 316.

Thus, the portions of the aerosol delivery device 100 (see, FIG. 1) most likely to be subjected to microbial growth and/or condensation formation from the aerosol include those surfaces surrounding and downstream of the atomizer 310 in terms of a flow path through the aerosol delivery device 100. For example, aerosol may condense at one or more inner surfaces 316A of the mouthpiece 316 and/or one or more inner surfaces 314A of the outer body 314. The inner surfaces 316A of the mouthpiece 316 and the inner surfaces 314A of the outer body 314 may also be subjected to microbial growth due to exposure to the user's breath and saliva and any pathogens therein. Microbial growth may additionally occur at the surfaces contacted by the user. In particular, an outer surface 316B of the mouthpiece 316 may be subjected to repeated contact with a user's lips and hence the outer surface may be subject to microbial growth.

Accordingly, in some embodiments the aerosol delivery device 100 (see, FIG. 1) may include features at the inner and outer surfaces 316A, 316B of the mouthpiece and the inner surfaces 314A of the outer body 314 configured to resist microbial growth. For example, in some embodiments these surfaces 316A, 316B, 314A may include a coating configured to address the above-noted problems. For example, the surfaces 316A, 316B, 314A may include an antimicrobial coating. Antimicrobial coatings are either configured to kill microorganisms or prohibit their growth. Thereby, usage of an antimicrobial coating may address issues with respect to microbial growth in or on the aerosol delivery device. Further, as noted above, condensing of the aerosol may present issues. Accordingly, the selected coating may be hydrophobic. Hydrophobic surfaces may resist the formation of fluid droplets thereon, such that issues with respect to condensing of the aerosol may be mitigated. However, usage of an antimicrobial and/or hydrophobic coating may expose the user to the chemicals in such coatings. In this regard, some coatings having antimicrobial and/or hydrophobic properties may be toxic. Further, coatings may wear off during usage such that the efficacy thereof may diminish.

For these reasons usage of a coating to address the issues with respect to microbial growth and/or aerosol condensation may be less than optimal. Thus, embodiments of the present disclosure are directed to aerosol delivery devices and components thereof configured to resist microbial growth and/or resist condensing of aerosol without the use of a coating applied to the surfaces thereof.

Thus, embodiments of the present disclosure are directed to an aerosol production assembly including a surface with engineered hydrophobic and/or anti-microbial properties. In other words, the surface can include three-dimensional structures imparting hydrophobic and/or anti-microbial characteristics to the surface. For the reasons noted above, the surface may expressly exclude a chemical coating, particularly chemical anti-microbial coatings.

Rather, the surface of the aerosol production assembly may comprise a micro-pattern. In this regard, a micro-pattern can refer to an engineered surface topography including ordered three-dimensional features at the micrometer scale. Such a surface may be distinguished from inherent surface features of objects at least on the basis of the three-dimensional pattern being specifically, intentionally formed to define the ordered pattern at the micro-meter scale. As described below, in some embodiments the micro-pattern may comprise a biomimicry micro-pattern configured to mimic the surface topography of certain surfaces of natural organisms that provide anti-microbial and/or hydrophobic properties, which further distinguishes the present micro-patterns from inherent surface topographies of objects.

The micro-pattern can exhibit a variety of geometries (e.g., pillars, channels, platelets, cones, divots, etc.) and can be specifically engineered with a defined roughness, which can provide specific biological responses and/or can control bioadhesion. The micro-pattern can be substantially constant (e.g., exhibiting a single, repeating feature of substantially unchanging dimensions) and/or can exhibit a substantially repeating pattern (e.g., a plurality of features differing in one or more of size, shape, and spacing, that define an ordered, repeating pattern). The micro-pattern may be defined at least in part in relation to the size and/or spacing of the geometric elements forming the micro-pattern. For example, the geometric elements can have an average height of about 1 µm to about 500 µm, about 1.5 µm to about 250 µm, about 2 µm to about 100 µm, about 2.5 µm to about 50 µm, or about 3 µm to about 25 µm. The geometric elements can have an average spacing of about 0.1 µm to about 20 µm, about 0.25 µm to about 15 µm, about 0.5 µm to about 10 µm, or about 1 µm to about 5 µm. Usage of a surface having a micro-pattern so as to be hydrophobic may resist buildup of biological matter thereon and may resist the formation of condensation thereon, thereby addressing the above-noted issues with respect to microbial growth and condensation.

As noted above, a surface may be provided with a micro-pattern to impart at least one of hydrophobic and anti-microbial properties thereto. The surface including the micro-pattern may be positioned at an inner surface of the aerosol production assembly. For example, the surface including a micro-pattern may be provided at the inner surface(s) 316A of the mouthpiece 316 and/or at the inner surface(s) 314A of the outer body 314. Additionally or alternatively, the surface including a micro-pattern may be positioned at an outer surface of the aerosol production assembly. For example, the surface including a micro-pattern may be provided at the outer surface 316B of the mouthpiece 316. Accordingly, the surface including a micro-pattern may be positioned at the surfaces noted above at which microbial growth and/or condensing of the aerosol may occur. As may be understood, the surface including a micro-pattern may be provided at any surface of the aerosol delivery device 100 (see, FIG. 1).

Various embodiments of surfaces including a micro-pattern may be employed. In one or more embodiments, however, it can be desirable for the micro-pattern to substantially mimic a micro-pattern found in nature. In other words, the micro-pattern may be substantially an engineered replicant of a natural, microscale topographical pattern or a biomimicry micro-pattern. As an example, sharkskin is known to be highly resistant to the attachment of living organisms such as barnacles and algae thereto. Further, sharkskin may be hydrophobic. Such attachment resistance and water resistance may be provided at least in part by a topographical pattern on the skin defining a rough surface.

An microscopic image of sharkskin 500 is illustrated in FIG. 5. As illustrated, the sharkskin comprises a matrix of hard, tooth-like structures 502 called dermal denticles or placoid scales. The tooth-like structures 502 may define a pattern of diamond or parallelogram shapes 504 at the locations where the tooth-like structures are exposed. Each tooth-like structure 502 may include a plurality of raised parallel ribs 506 separated by recesses 508.

One embodiment of a surface including a micro-pattern 600 is illustrated in FIG. 6. The surface including a micro-pattern 600 may be employed at any of the surfaces of the aerosol delivery device 100 such as the surfaces particularly noted above that may be subject to microbial growth or condensation formation. As illustrated, the micro-pattern 600 is a biomimicry micro-pattern that is substantially a sharkskin micro-pattern. In this regard, the surface including a micro-pattern 600 may include a pattern of diamond or parallelogram shapes 604. The parallelograms 604 may define a width from about twenty micrometers to about thirty micrometers. Each parallelogram 604 may include a plurality of raised parallel ribs 606 separated by recesses 608. The ribs 606 may extend from about two micrometers to about four from micrometers outwardly from the recesses 608. Accordingly, the surface including a micro-pattern 600 defining the sharkskin micro-pattern may embody properties resembling those of natural sharkskin. Thus, for example, the surface including a micro-pattern 600 defining the sharkskin micro-pattern may provide anti-microbial and/or hydrophobic properties. Example embodiments of products including a sharkskin micro-pattern are available from Sharklet Technologies, Inc. of Aurora, Colo. Surface topographies suitable for use as a micro-pattern according to embodiments of the present disclosure are described in U.S. Pat. No. 8,997,672 to Brennan et al., which is incorporated herein by reference in its entirety.

Various other embodiments of surfaces including a micro-pattern may be employed. In this regard, the lotus leaf defines superhydrophobic properties, which may resist the buildup of water and matter thereon. The superhydrophobic properties are provided in part by an epicuticular wax. However, the superhydrophobic properties may be additionally provided by the structure of the surface thereof. In this regard, FIG. 7 is a scanning electron microscope (SEM) image of a lotus leaf 700 at scales of five micrometers and fifty micrometers. As illustrated, the lotus leaf 700 may include a plurality of papillae 702. The papillae 702 may define a height from about ten to about twenty micrometers and a width from about ten to about fifteen micrometers.

FIG. 8 is a scanning electron microscope image of an additional embodiment of a surface including a micro-pattern 800 at scales of five micrometers and fifty micrometers. As illustrated, the micro-pattern 800 is a biomimicry micro-pattern that is substantially a lotus leaf micro-pattern. In this regard, the surface including a micro-pattern may include a plurality of protrusions 802 that mimic the size and shape of the papillae 702 of the lotus leaf 700 (see, FIG. 7). For example, the protrusions 802 may define a height from about ten to about twenty micrometers and a width from about ten to about fifteen micrometers. Additional description with respect to surfaces including a lotus leaf micro-pattern is provided in *Superhydrophobic Surfaces Developed by Mimicking Hierarchical Surface Morphology of Lotus Leaf* by Latthe et al., which is incorporated herein by reference in its entirety.

Accordingly, the surface including a micro-pattern 800 defining the lotus leaf micro-pattern may embody properties resembling those of a natural lotus leaf. Thus, for example, the surface including a micro-pattern 800 defining the lotus leaf micro-pattern may provide anti-microbial and/or hydrophobic properties.

Note that although the surface including a micro-pattern is generally described herein as being employed in embodiments of aerosol delivery devices including cartridges, it should be understood that the surface including a micro-pattern may be included in any embodiment of an aerosol delivery device. For example, FIG. 9 illustrates a sectional view through a tank 900 for an aerosol delivery device. The tank 900 may include a base 902, a control component terminal 904, an electronic control component 906, a flow director 908 which may be defined by an outer body 912 or a separate component, an atomizer 910, and a mouthpiece 914 according to an example embodiment of the present disclosure. The atomizer 910 may comprise a first heating terminal 916a and a second heating terminal 916b, a liquid transport element 918 and a heating element 920. The tank 900 may additionally include a base shipping plug, a label, and a mouthpiece shipping plug, as described above.

The base 902 may be coupled to a first end of the outer body 912 and the mouthpiece 914 may be coupled to an opposing second end of the outer body to at least partially enclose the remaining components of the tank 900 therein. In some embodiments the base 902 may comprise antirotation features that substantially prevent relative rotation between the tank and associated device including a power source as disclosed in U.S. Pat. App. Pub. No. 2014/0261495 to Novak et al., which is incorporated herein by reference in its entirety.

The tank 900 may further comprise a sealing member 922 and an initial liquid transport element 924. In this regard, the outer body 912 and/or an additional component may be configured to hold an aerosol precursor composition 926 in a reservoir 928. In some embodiments the reservoir 928 may be configured to be refillable, whereas in other embodiments the tank 900 may be configured for a single use. The sealing member 922 may be positioned at an end of the chamber 928 and include one or more apertures 930 that allow the aerosol precursor composition 926 to contact the initial liquid transport element 924. Further, the liquid transport element 918 of the atomizer 910 may be in contact with the initial liquid transport element 924. Both the initial liquid transport element 924 and the liquid transport element 918 of the atomizer 910 may comprise wicking and/or porous materials that allow movement of the aerosol precursor composition 926 therethrough (e.g., via capillary action), such that the aerosol precursor composition may be drawn to the heating element 920 and heated and vaporized when current is applied to the heating element via the heating terminals 916a, 916b by a control body.

Accordingly, the tank 900 may include an aerosol production assembly. Aerosol may be produced at the atomizer 910 and directed through the flow director 908, the outer body 912, and the mouthpiece 914 to the user. Thus, by way of example an inner surface 908A of the flow director 908, an inner surface 912A of the outer body 912, and/or an inner surface 914A of the mouthpiece 914 may comprise a surface of which at least a portion includes a micro-pattern, and the micro-pattern may have anti-microbial and/or hydrophobic properties. Further, an outer surface 914B of the mouthpiece 914 may comprise a surface of which at least a portion includes a micro-pattern, and the micro-pattern may have anti-microbial and/or hydrophobic properties. Accordingly, embodiments of the present disclosure include aerosol production assemblies included in a cartridge or a tank for an aerosol delivery device, or any other embodiment of an aerosol delivery device or portion thereof.

Various embodiments of methods may be employed to form the surfaces including a micro-pattern of the present disclosure. In one example method, one or more components of the aerosol delivery device 100 (see, FIG. 1) may be formed in a mold configured to define the surface including a micro-pattern. The mold may be etched (e.g., chemical, electrochemical, or laser etched) to define a surface configured to form the surface including a micro-pattern. However, various other embodiments of methods for forming the surface including a micro-pattern may be employed. For example, the surface including a micro-pattern may be produced by one or more methods such as self-assembly of a monolayer, photolithography, plasma polymerization, ultraviolet illumination, electrospinning, irradiation, template methods, chemical deposition, and blasting (e.g., with sodium bicarbonate) followed by anodizing the blasted surface. Various examples of such methods for producing surfaces including a micro-pattern are described in *Artificial Lotus Leaf Structures Made by Blasting with Sodium Bicarbonate* by Lee et al., which is incorporated herein by reference in its entirety.

Thus, various methods may be used for forming a micro-pattern as described herein. For example, patterning may be via an additive technique or a reductive technique. In an additive technique, a material may be deposited on the surface to form the pattern. The patterning material may be identical in composition to the thin film or may be of a different composition. In a reductive technique, a portion of the surface may be removed to form a series of grooves defining the micro-pattern. Non-limiting examples of patterning techniques that are encompassed by the present disclosure include nanoimprinting, photolithography, electron beam, ion beam, x-ray, self-assembly, lift-off, and similar patterning methods.

FIG. 10 illustrates a method for assembling an aerosol production assembly. As illustrated, the method may include providing an aerosol precursor composition at operation 1002. The method may additionally include positioning an atomizer in fluid communication with the aerosol precursor composition. Further, the method may include assembling the atomizer with a body comprising a surface of which at least a portion includes a micro-pattern imparting at least one of hydrophobic and anti-microbial properties.

Assembling the atomizer with the body at operation 1006 may include positioning the body in fluid communication with the atomizer. The method may further include forming the body including the micro-pattern. Forming the body may not include coating the surface with a chemical. Forming the body may include forming the micro-pattern at least one of an inner surface and an outer surface of the body. Additionally, forming the body may include forming the micro-pattern in a mold. The method may further include etching the mold.

FIG. 11 illustrates a method of improving cleanliness of an aerosol delivery device. As illustrated, the method may include providing the aerosol delivery device with a surface of which at least a portion includes a micro-pattern imparting at least one of hydrophobic and anti-microbial properties at operation 1102. In some embodiments the micro-pattern may be a biomimicry micro-pattern. The surface may define a sharkskin micro-pattern or a lotus leaf micro-pattern.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An aerosol production assembly comprising:
an aerosol precursor composition;
an atomizer configured to produce aerosol from the aerosol precursor composition; and
a body comprising a mouthpiece defining an outlet and a surface, at least a portion of the surface being an inner surface of the mouthpiece and the body, of which at least a portion of the surface, including the inner surface of the mouthpiece and the body includes a biomimicry micro-pattern that is an engineered surface topography including ordered three-dimensional features at the micro-meter scale and that mimics a surface topography of a surface of a natural organism so as to impart anti-microbial properties and resist microbial growth, wherein the surface does not include a chemical anti-microbial coating, the aerosol from the atomizer being directed to the outlet by way of transport through the body, and the mouthpiece and being in contact with the respective inner surfaces of the body and the mouthpiece.

2. The aerosol production assembly of claim 1, wherein the surface defines a sharkskin micro-pattern or a lotus leaf micro-pattern.

3. The aerosol production assembly of claim 1, wherein at least another portion of the surface is positioned at an outer surface of the body.

4. The aerosol production assembly of claim 1, wherein the body is formed in a mold configured to define the biomimicry micro-pattern at the surface.

5. The aerosol production assembly of claim 4, wherein the mold is etched.

6. The aerosol production assembly of claim 1, wherein the aerosol production assembly is included in a cartridge or a tank for an aerosol delivery device.

7. A method of forming an aerosol production assembly, the method comprising:
providing an aerosol precursor composition;
positioning an atomizer in fluid communication with the aerosol precursor composition to produce aerosol from the aerosol precursor composition;
forming a body including a biomimicry micro-pattern, wherein forming the body does not include coating a surface of the body with a chemical anti-microbial coating; and
assembling the atomizer with the body comprising a mouthpiece defining an outlet and a surface, at least a portion of the surface being an inner surface of the mouthpiece and the body, wherein at least a portion of the surface, including the inner surface of the mouthpiece and the body, includes the biomimicry micro-pattern that is an engineered surface topography including ordered three-dimensional features at the micrometer scale and that mimics a surface topography of a surface of a natural organism so as to impart anti-microbial properties and resist microbial growth, the aerosol from the atomizer being directed to the outlet by way of transport through the body and the mouthpiece, and being in contact with the respective inner surfaces of the body and the mouthpiece.

8. The method of claim 7, wherein assembling the atomizer with the body comprises positioning the body in fluid communication with the atomizer.

9. The method of claim 7, wherein forming the body comprises forming the biomimicry micro-pattern at an outer surface of the body.

10. The method of claim 7, wherein forming the body comprises forming the biomimicry micro-pattern in a mold.

11. The method of claim 10, further comprising etching the mold.

12. A method of improving cleanliness of an aerosol delivery device including an atomizer configured to produce aerosol from an aerosol precursor composition, the method comprising:
providing the aerosol delivery device with a surface of which at least a portion of the surface is an inner surface of a body and a mouthpiece of the body defining an outlet, of which at least a portion of the surface, including the inner surface of the mouthpiece and the body, includes a biomimicry micro-pattern that is an engineered surface topography including ordered three-dimensional features at the micro-meter scale and that mimics a surface topography of a surface of a natural organism so as to impart anti-microbial properties and resist microbial growth, wherein the surface does not include a chemical anti-microbial coating, the aerosol from the atomizer being directed to the outlet by way of transport through the body and the mouthpiece, and being in contact with the respective inner surfaces of the body and the mouthpiece.

13. The method of claim 12, wherein the surface defines a sharkskin micro-pattern or a lotus leaf micro-pattern.

14. The aerosol production assembly of claim 1, wherein the engineered surface topography of the biomimicry micro-pattern is arranged to resist condensing of an aerosol.

15. The method of claim 7, wherein the engineered surface topography of the biomimicry micro-pattern is arranged to resist condensing of an aerosol.

16. The method of claim 12, wherein the engineered surface topography of the biomimicry micro-pattern is arranged to resist condensing of an aerosol.

* * * * *